US007439028B2

(12) United States Patent
Alderete et al.

(10) Patent No.: US 7,439,028 B2
(45) Date of Patent: Oct. 21, 2008

(54) **METHODS AND COMPOSITIONS TO CORRELATE *TRICHOMONAS* INFECTION WITH PROSTATE CANCER**

(75) Inventors: John F. Alderete, San Antonio, TX (US); Te-Hung Chang, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 11/519,708

(22) Filed: Sep. 12, 2006

(65) Prior Publication Data

US 2007/0077606 A1 Apr. 5, 2007

Related U.S. Application Data

(60) Provisional application No. 60/726,330, filed on Oct. 13, 2005, provisional application No. 60/722,381, filed on Sep. 30, 2005.

(51) Int. Cl.
*G01N 33/53* (2006.01)
*G01N 33/574* (2006.01)

(52) U.S. Cl. .................... 435/7.1; 435/7.23; 435/7.8

(58) Field of Classification Search .............. None
See application file for complete search history.

(56) References Cited

U.S. PATENT DOCUMENTS

| | | | |
|---|---|---|---|
| 4,514,498 A | 4/1985 | Kettman et al. | |
| 4,707,442 A | 11/1987 | Alderete | |
| 4,861,711 A | 8/1989 | Friesen et al. | |
| 5,004,694 A | 4/1991 | Moay et al. | |
| 5,037,615 A | 8/1991 | Kane | |
| 5,330,897 A | 7/1994 | Pindak et al. | |
| 5,369,005 A | 11/1994 | Baseman et al. | |
| 5,415,994 A | 5/1995 | Imrich et al. | |
| 5,516,638 A | 5/1996 | Urnovitz et al. | |
| 5,679,551 A | 10/1997 | Alderete | |
| 5,741,662 A | 4/1998 | Madsen et al. | |
| 5,776,694 A | 7/1998 | Sheiness et al. | |
| 5,876,985 A | 3/1999 | Alderete | |
| 5,879,881 A | 3/1999 | Rubenstein | |
| 5,922,563 A | 7/1999 | Alderete | |
| 6,063,905 A | 5/2000 | Capra et al. | |
| 6,174,293 B1 | 1/2001 | Buck et al. | |
| 6,207,395 B1 | 3/2001 | Valkirs et al. | |
| 6,528,321 B1 | 3/2003 | Fitzgerald et al. | |
| 6,824,975 B2 | 11/2004 | Hubscher et al. | |
| 2002/0045195 A1 | 4/2002 | Hubscher et al. | |
| 2003/0032029 A1 | 2/2003 | Collins | |
| 2003/0073147 A1 | 4/2003 | Alderete | |
| 2004/0072280 A1 | 4/2004 | Lawerence et al. | |
| 2007/0009974 A1 | 1/2007 | Alderete et al. | |
| 2007/0015224 A1 | 1/2007 | Alderete et al. | |
| 2007/0134741 A1 | 6/2007 | Alderete et al. | |

FOREIGN PATENT DOCUMENTS

| | | |
|---|---|---|
| EP | 0 050 424 B1 | 4/1982 |
| EP | 0 810 436 A1 | 12/1997 |
| WO | WO 92/07096 A1 | 4/1992 |
| WO | WO 03/009814 A2 * | 2/2003 |

OTHER PUBLICATIONS

Sutcliffe, S., Giovannucci, E., Alderete, J.F., Chang, T., Gaydos, G.A., Zenilman, J.M., De Marzo, A.M., Willett, W.C., and Platz, E.A. Plasma antibodies against *Trichomonas vaginalis* and subsequent risk of prostate cancer. Cancer Epidemiology Biomarkers and Prevention, 2006. vol. 15 No. 5, pp. 939-945.*

Addis et al. "Host and Tissue Specificity of *Trichomonas vaginalis* Is Not Mediated by Its Known Adhesion Proteins" *Infection and Immunity* 68(7):4358-4360 (2000).

Addis et al. "Cloning and Molecular Characterization of a cDNA Clone Coding for *Trichomonas vaginalis* Alpha-Actinin and Intracellular Localization of the Protein" *Infection and Immunity* 66(10):4924-4931 (1998).

Alderete and Garza "Soluble *Trichomonas vaginalis* Antigens in Cell-Free Culture Supernatants" *Molecular and Biochemical Parasitology* 13: 147-158 (1984).

Alderete et al. "Cloning and Molecular Characterization of Two Genes Encoding Adhesion Proteins Involved in *Trichomonas vaginalis* Cytoadherence" *Molecular Microbiology* 17(1):69-83 (1995).

Alderete et al. "Monoclonal Antibody to a Major Surface Glycoprotein Immunogen Differentiates Isolates and Subpopulations of *Trichomonas vaginalis*" *Infection and Immunity* 52(1):70-75 (1986).

(Continued)

*Primary Examiner*—David J. Blanchard
*Assistant Examiner*—Anne M. Gussow
(74) *Attorney, Agent, or Firm*—Myers Bigel Sibley & Sajovec, P.A.

(57) ABSTRACT

The present invention provides methods and compositions for identifying a subject at increased risk of having prostate cancer by detecting an antibody that specifically binds a *Trichomonas* α-actinin protein in a sample of the subject.

4 Claims, No Drawings

OTHER PUBLICATIONS

Alderete et al. "Phenotypes and Protein-Epitope Phenotypic Variation Among Fresh Isolates of *Trichomonas vaginalis*" *Infection and Immunity* 55(5):1037-1041 (1987).

Alderete et al. "Specific Parasitism of Purified Vaginal Epithelial Cells by *Trichomonas vaginalis*" *Infection and Immunity* 56(10):2558-2562 (1988).

Alderete "Identification of Immunogenic and Antibody-Binding Membrane Proteins of Pathogenic *Trichomonas vaginalis*" *Infection and Immunity* 40(1):284-291 (1983).

Alderete and Garza "Identification and Properties of *Trichomonas vaginalis* Proteins Involved in Cytadherence" *Infection and Immunity* 56(1):28-33 (1988).

Alderete and Kasmala "Monoclonal Antibody to a Major Glycoprotein Immunogen Mediates Differential Complement-Independent Lysis of *Trichomonas vaginalis*" *Infection and Immunity* 53(3):697-699 (1986).

Alderete et al. "Heterogeneity of *Trichomonas vaginalis* and Discrimination among Trichomonal Isolates and Subpopulations with Sera of Patients and Experimentally Infected Mice" *Infection and Immunity* 49(3):463-468 (1985).

Alderete et al. "Phenotypic Variation and Diversity Among *Trichomonas vaginalis* Isolates and Correlation of Phenotype with Trichomonal Virulence Determinants" *Infection and Immunity* 53(2):285-293 (1986).

Alderete et al. "Only two of the *Trichomonas vaginalis* triplet AP51 adhesins are regulated by iron" *Microbial Pathogenesis* 24:1-16 (1998).

Alderete et al. "*Trichomonas vaginalis* Genetic Analysis of Cell Adherence" Abstract from CRISP website for Grant No. 2R21AI043940-05, Fiscal year 2003.

Alonzo and Pepe "Using a Combination of Reference Tests to Assess the Accuracy of a New Diagnostic Test" *Statistics in Medicine* 18:2987-3003 (1999).

Arroyo et al. "Molecular Basis of Host Epithelial Cell Recognition by *Trichomonas vaginalis*" *Molecular Microbiology* 6(7):853-862 (1992).

Arroyo et al., "Signalling of *Trichomonas vaginalis* for Amoeboid Tranformation and Adhesin Synthesis Follows Cytoadherence" *Molecular Microbiology* 7(2):299-309 (1993).

Arroyo et al. "Characterization of cDNAs Encoding Adhesin Proteins Involved in *Trichomonas vaginalis* Cytoadherence" *Archives of Medical Research* 26(4):361-369 (1995).

Baseman et al. "San Antonio STI TM CRC" Abstract from the CRISP website for Grant No. 2U19AI045429-06, Fiscal year 2004.

Benchimol et al. "Structure and Division of the Golgi Complex in *Trichomonas vaginalis* and *Tritrichomonas foetus*" *European Journal of Cell Biology* 80:593-607 (2001).

Bricheux et al. "Evidence for an uncommon α-actinin protein in *Trichomonas vaginalis*" *Molecular and Biochemical Parasitology* 95:241-249 (1998).

Checkoway et al. "Medical, Life-Style, and Occupational Risk Factors for Prostate Cancer" *The Prostate* 10:79-88 (1987).

Cogne et al. "Detection and Characterization of Serum Antitrichomonal Antibodies in Urogential Trichomoniasis" *Journal of Clinical Microbiology* 21(4): 588-592 (1985).

Cuatrecasas, Pedro "Protein Purification by Affinity Chromatography" *The Journal of Biological Chemistry* 245(12): 3059-3065 (1970).

Dalchau et al. "Monoclonal Antibody to a Human Leukocyte-Specific Membrane Glycoprotein Probably Homologous to the Leukocyte-Common (L-C) Antigen of the Rat" *Eur. J. Immunol.* 10:737-744 (1980).

Dennis et al. "Meta-Analysis of Measures of Sexual Activity and Prostate Cancer" *Epidemiology* 13:72-79 (2002).

Engbring et al. "Three genes encode distinct AP33 proteins involved in *Trichomonas vaginalis* cytoadherence" *Molecular Microbiology* 28(2):305-313 (1998).

Engbring et al. "Characterization of *Trichomonas vaginalis* AP33 adhesin and cell surface interactive domains" *Microbiology* 144:3011-3018 (1998).

Estrada et al. "Reporting and Concordance of Methodologic Criteria Between Abstracts and Articles in Diagnostic Test Studies" *JGIM* 15:183-187 (2000).

European Search Report for EP 03746064.9; dated Mar. 22, 2007.

Garber et al. "Immunogenic Proteins of *Trichomonas vaginalis* as Demonstrated by the Immunoblot Technique" *Infection and Immunity* 51(1):250-253 (1986).

Garber et al. "Cell Culture Compared with Broth for Detection of *Trichomonas vaginalis*" *Journal of Clinical Microbiology* 25(7):1275-1279 (1987).

Genzyme Diagnostics Product Information Sheet for OSOM *Trichomonas* Rapid Test. Printed from Genzyme website, Apr. 2007.

Hobbs et al. "Methods for Detection of *Trichomonas vaginalis* in the Male Partners of Infected Women: Implications for Control of Trichomoniasis" *Journal of Clinical Microbiology* 44(11):3994-3999 (2006).

Huppert et al. "Use of an immunochromatographic assay for rapid detection of *Trichomonas vaginalis* in vaginal samples" *J. Clin. Microbiol.* 43(2):684-687 (2005).

Huse et al. "Generation of a Large Combinatorial Library of the Immunoglobulin Repertoire in Phage Lambda" *Science* 246: 1275-1281 (1989).

International Search Report corresponding to International application No. PCT/US03/09474, mailed Jul. 21, 2003.

Köhler and Milstein "Continuous Cultures of Fused Cells Secreting Antibody of Predefined Specificity" *Nature* 256:495-497 (1975).

Krieger et al. "Clinical Manifestations of Trichomoniasis in Men" *Annals of International Medicine* 118(11):844-849 (1993).

Kuberski et al. "Ankylosing Spondylitis Associated with *Trichomonas vaginalis* Infection" *Journal of Clinical Microbiology* 13(5):880-881.

Kucknoor et al. "Adherence to Human Vaginal Epithelial Cells Signals for Increased Expression of *Trichomonas vaginalis* Genes" *Infection and Immunity* 73(10):6472-6478 (2005).

Lehker et al. "The Regulation by Iron of the Synthesis of Adhesins and Cytoadherence Levels in the Protozoan *Trichomonas vaginalis*" *J. Exp. Med.* 174:311-318 (1991).

Lehker and Sweeney "Trichomonad Invasion of the Mucous Layer Requires Adhesins, Mucinases, and Motility" *Sex. Transm. Inf.* 75:231-238 (1999).

Lisi et al. "Monoclonal-Antibody-Based Enzyme-Linked Immunosorbent Assay for *Trichomonas vaginalis*" *Journal of Clinical Microbiology* 26(9):1684-1686 (1988).

Matthews et al. "Evaluation of Two Serological Tests for *Trichomonas vaginalis* Infection" *Journal of Clinical Microbiology* 17(5):840-843 (1983).

Miller et al. "Assessment of a rapid antigen detection system for *Trichomonas vaginalis* infection" *Clinical and Diagnostic Laboratory Immunology* 10(6):1157-8 (2003).

Mohamed et al. "Urine proves a poor specimen for culture of *Trichomonas vaginalis* in women" *Sex. Transm. Infect.* 77(1):78-79 (2001).

O'Brien et al. "Molecular Characterization of a Third Malic Enzyme-Like AP65 Adhesin Gene of *Trichomonas vaginalis*" *Microbial Pathogenesis* 20:335-349 (1996).

Patel et al. "Systematic Review of Diagnostic Tests for Vaginal Trichomoniasis" *Infectious Diseases in Obstetrics and Gynecology* 8:248-257 (2000).

Planned Parenthood Report "XenoStrip™-Tv *Trichomonas* Test Clinical Efficacy Assessment" Xenotrope Diagnostics, Inc. Jan. 22, 2004.

Ponce De Leon et al. "Relation Between Buccal Protozoa and pH and Salivary IgA in Patients with Dental Prothesis" *Rev. Inst. Med. Trop. S. Paulo* 43(4):241-242 (2001).

Rappelli et al. "Sequence of cDNA coding for a 65 kDa adhesive protein for the specific detection of *Trichomonas vaginalis* by PCR" *FEMS Microbiology Letters* 129:21-26 (1995).

Rosenblatt et al. "Sexual Factors and the Risk of Prostate Cancer" *American Journal of Epidemiology* 153(12):1152-1158 (2001).

Stary et al. "Detection of *Trichomonas vaginalis* on Modified Columbia Agar in the Routine Laboratory" *Journal of Clinical Microbiology* 40(9):3277-3280 (2002).

Sutcliffe et al. "Plasma antibodies against *Trichomonas vaginalis* and subsequent risk of prostate cancer" Abstract of poster presented at the 4th Annual American Association for Cancer Research International Conference entitled "Frontiers in Cancer Prevention Research." Baltimore, MD, Oct. 30-Nov. 2, 2005.

Sutcliffe et al. "Plasma antibodies against *Chlamydia trachomatis*, human papillomavirus, and human herpesvirus type 8 in relation to prostate cancer: a prospective study" *Cancer Epidemiol Biomarkers Prev.* 16(8):1573-80 (2007).

van der Schee et al. "Improved Diagnosis of *Trichomonas vaginalis* Infection by PCR Using Vaginal Swabs and Urine Specimens Compared to Diagnosis by Wet Mount Microscopy, Culture, and Flourescent Staining" *Journal of Clinical Microbiology* 37(12):4127-4130 (1999).

Wasserheit "Epidemiological Synergy: Interrelationships between Human Immunodeficiency Virus Infection and Other Sexually Transmitted Diseases" *Jn. Sex. Trans. Dis.* 19:61-77 (1992).

Watson-Jones et al. "High prevalence of trichomoniasis in rural men in Mwanza, Tanzania: results from a population based study" *Sex. Transm. Inf.* 76:355-362 (2000).

Watt et al. "Rapid Assay for Immunological Detection of *Trichomonas vaginalis*" *Journal of Clinical Microbiology* 24(4):551-555 (1986).

Wiese et al. "A meta-analysis of the Papanicolaou smear and wet mount for the diagnosis of vaginal trichomoniasis" *The American Journal of Medicine* 108(4):301-308 (1999).

Wos et al. "Immunoglobulin Isotypes of Anti-*Trichomonas vaginalis* Antibodies in Patients with Vaginal Trichomoniasis" *Journal of Clinical Microbiology* 24(5):790-795 (1986).

Yap et al. "Serum Antibodies to *Trichomonas vaginalis* in Invasive Cervical Cancer Patients" *Genitourin Med.* 71:402-404 (1995).

Zhang et al. "*Trichomonas vaginalis* and Cervical Cancer: A Prospective Study in China" *Ann. Epidemiol.* 5(4):325-332 (1995).

* cited by examiner

METHODS AND COMPOSITIONS TO CORRELATE *TRICHOMONAS* INFECTION WITH PROSTATE CANCER

STATEMENT OF PRIORITY

This application claims the benefit, under 35 U.S.C. § 119(e), of U.S. Provisional Application No. 60/722,381, filed Sep. 30, 2005 and U.S. Provisional Application No. 60/726,330, filed Oct. 13, 2005, the entire contents of each of which are incorporated by reference herein in their entireties.

BACKGROUND OF THE INVENTION

*Trichomonas vaginalis* causes vaginitis in women and non-gonococcal non-chlamydial urethritis in men. An estimated 5 million new cases of trichomonosis occur each year in the US, the majority in women. This sexually transmitted infection (STI) is associated with adverse outcomes in pregnancy. In addition, this STI may be associated with cervical cancer. Significantly, African Americans have the highest rates of trichomonosis than other American communities, and this STI contributes to the spread of HIV among women and minorities in the US. Epidemiologic studies suggest that *Trichomonas vaginalis* is associated with a 2- to 4-fold increased risk of HIV transmission, contributing to health disparities, and control of trichomonosis may be one of the most effective means of reducing HIV transmission risk worldwide.

Furthermore, previous studies have demonstrated a correlation between a history of STIs such as gonorrhea and syphilis and prostate cancer (1), but no comprehensive study has previously been carried out to demonstrate a link between prostate cancer or an increased likelihood of prostate cancer and immunological evidence of *Trichomonas* infection. Thus, the present invention overcomes previous shortcomings in the art by providing methods and compositions for identifying male subjects at increased risk of having prostate cancer on the basis of a history of *Trichomonas vaginalis* infection.

SUMMARY OF THE INVENTION

The present invention provides a method of identifying a subject at increased risk of developing prostate cancer, comprising: a) contacting a sample from the subject with a *Trichomonas* α-actinin protein under conditions whereby an antigen/antibody complex can form; and b) detecting formation of an antigen/antibody complex, thereby detecting an antibody that specifically binds a *Trichomonas* α-actinin protein in the sample and thereby identifying a subject at increased risk of developing prostate cancer.

In additional embodiments, the present invention provides a method of diagnosing prostate cancer in a subject, comprising: a) contacting a sample from the subject with a *Trichomonas* α-actinin protein under conditions whereby an antigen/antibody complex can form; and b) detecting formation of an antigen/antibody complex, thereby detecting an antibody that specifically binds a *Trichomonas* α-actinin protein in the sample and thereby diagnosing prostate cancer in the subject.

Also provided is a method of diagnosing prostate cancer in a subject and/or identifying a subject at increased risk of having or developing prostate cancer, comprising: a) contacting a sample from the subject with an antibody that specifically binds a *Trichomonas* α-actinin protein under conditions whereby an antigen/antibody complex can form; and b) detecting formation of an antigen/antibody complex, thereby detecting a *Trichomonas* α-actinin protein and thereby diagnosing prostate cancer in the subject and/or identifying the subject at increased risk of having prostate cancer.

DETAILED DESCRIPTION OF THE INVENTION

As used herein, "a" or "an" or "the" can mean one or more than one. For example, "a" cell can mean one cell or a plurality of cells.

Also as used herein, "and/or" refers to and encompasses any and/or all possible combinations of one or more of the associated listed items, as well as the lack of and and/or combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The present invention is based on the unexpected discovery of a correlation between prostate cancer and *Trichomonas* (e.g., *Trichomonas vaginalis*) infection as detected by the presence of *Trichomonas* α-actinin antibody and/or antigen in a subject.

Thus, in some embodiments of this invention, a method is provided, of diagnosing prostate cancer in a subject, comprising: a) contacting a sample from the subject with a *Trichomonas* α-actinin protein under conditions whereby an antigen/antibody complex can form; and b) detecting formation of an antigen/antibody complex, thereby detecting an antibody that specifically binds a *Trichomonas* α-actinin protein in the sample and thereby diagnosing prostate cancer in the subject.

In addition, the present invention provides a method of identifying a subject at increased risk of having or developing prostate cancer, comprising: a) contacting a sample from the subject with a *Trichomonas* α-actinin protein under conditions whereby an antigen/antibody complex can form; and b) detecting formation of an antigen/antibody complex, thereby detecting an antibody that specifically binds a *Trichomonas* α-actinin protein in the sample and thereby identifying a subject at increased risk of having or developing prostate cancer.

Also provided is a method of diagnosing prostate cancer in a subject, comprising: a) contacting a sample from the subject with an antibody that specifically binds a *Trichomonas* α-actinin protein under conditions whereby an antigen/antibody complex can form; and b) detecting formation of an antigen/antibody complex, thereby detecting a *Trichomonas* α-actinin protein and thereby diagnosing prostate cancer in the subject.

Also provided is a method of identifying a subject at increased risk of having or developing prostate cancer, comprising: a) contacting a sample from the subject with an antibody that specifically binds a *Trichomonas* α-actinin protein under conditions whereby an antigen/antibody complex can form; and b) detecting formation of an antigen/antibody complex, thereby detecting a *Trichomonas* α-actinin protein and thereby identifying the subject at increased risk of having or developing prostate cancer.

In the methods described herein for diagnosing prostate cancer and/or identifying a subject at increased risk of having or developing prostate cancer, a sample from the subject is tested for the presence of *Trichomonas* α-actinin antibody and/or antigen, which is indicative of either a past and/or current infection with *Trichomonas*. Follow up studies can then be carried out on additional samples from the subject to make a definitive diagnosis of prostate cancer or to identify a precancerous stage or condition that could develop or is developing into prostate cancer. Once a subject has been identified as having a current and/or past *Trichomonas* infection, he can be monitored over time for the development of prostate cancer according to protocols directed to subjects having increased risk of developing such a cancer.

A subject to be tested for the presence of *Trichomonas* α-actinin antibody and/or antigen is according to the methods of this invention is any male subject, including, for example, a male who is the sexual partner of a subject infected with *Trichomonas*, a male who is symptomatic for *Trichomonas* infection, a male subject who is asymptomatic for *Trichomonas* infection, a male with non-chlamydial non-gonococcal urethritis and/or a male with prostatitis, prostate neoplasia and/or prostate cancer.

In the methods of this invention, the sample can be any biological fluid or tissue that can be used in an immunoassay of this invention, including but not limited to, serum, plasma, blood, saliva, semen, cerebrospinal fluid, semen, prostatic fluid, urine, sputum, joint fluid, body cavity fluid, whole cells, cell extracts, tissue, biopsy material, aspirates, exudates, slide preparations, fixed cells, tissue sections, etc.

In particular embodiments of this invention, the antibody employed in the methods of this invention is an antibody that specifically binds a *Trichomonas* α-actinin protein. A non-limiting example of an antibody that specifically binds a *Trichomonas* α-actinin protein is monoclonal antibody HA423 (Kucknoor et al. 2005. "Adherence to human vaginal epithelial cells signals for increased expression of *Trichomonas vaginalis* genes." In press.) In certain embodiments, an antibody of this invention is not cross-reactive with human epithelial cell extracts or other protozoan protein extracts (e.g., *G. lambilia, E. histolytica, A. castellanii, L. major*). In further embodiments, an antibody of this invention has no, or minimal, crossreactivity with *T. tenax*. In yet other embodiments, an antibody of this invention does not bind or react with a *T. vaginalis* adhesin protein.

Furthermore, a *Trichomonas* protein of this invention can be, but is not limited to, a recombinant alpha actinin protein as described in the EXAMPLES section set forth herein, as well as peptides, fragments and immunologically similar variants of such proteins, peptides and fragments. Such proteins and peptides of this invention can be produced recombinantly according to methods well known in the art and can also be produced by fractionation and/or isolation techniques and/or synthesis techniques, etc. that are known for producing proteins and peptides for use in immunoassays.

The term "*Trichomonas*" or "*Trichomonas*" as used herein, includes, but is not limited to a protozoan parasite of the order Trichomonadida, genera *Ditrichomonas, Trichomonas, Tritrichomonas* and *Pentatrichomonas*, comprising multiple species that infect both humans and animals. "*Trichomonas*" refers to any *Trichomonas* species, e.g., *Tritrichomonas foetus* (also known as *Trichomonas foetus, Tt. fetus*), *Tt enteris* and *T. paviovi*, which infect cattle; *Tt. suis, Tt. rotunda* and *T. buttreyi*, which infect swine; *Dt. Ovis*, which infects sheep; *Tt. equi* and *T. equibuccalis*, which infect horses; *T. anatis, Tt. eberthi, T. gallinae* and *T. gallinarum*, which infect birds; *Tt. caviae, Tt muris, Tt. wenoni, Tt. Minuta* and *T. microti*, which infect rodents; *T. canistomae* and *T. felistomae*, which infect dogs and cats; and *T. tenax, T. vaginalis, Pt. hominis*, and *T. macacovaginae*, which infect primates (including humans). *Trichomonas vaginalis* as described herein includes isolate T016 (Type I) and isolate T068 (Type II), as well as any other *T. vaginalis* isolate now known or later identified.

The term "antibody" as used herein, includes, but is not limited to a polypeptide encoded by an immunoglobulin gene or immunoglobulin genes, or fragments thereof. "Antibody" also includes, but is not limited to, a polypeptide encoded by an immunoglobulin gene or immunoglobulin genes, or fragments thereof, which specifically binds to and recognizes the antigen-specific binding region (idiotype) of an antibody produced by the host in response to exposure to *Trichomonas* antigen(s).

The term "epitope" means an antigenic determinant that is specifically bound by an antibody. Epitopes usually consist of surface groupings of molecules such as amino acids and/or sugar side chains and usually have specific three-dimensional structural characteristics, as well as specific charge characteristics.

The terms "specifically binds to" and "specifically reactive with" refer to a binding reaction that is determinative of the presence of the antigen and antibody in the presence of a heterogeneous population of proteins and other biologics. Thus, under designated assay conditions, the specified antibodies and antigens bind to one another and do not bind in a significant amount to other components present in a sample. Specific binding to a target analyte under such conditions may require a binding moiety that is selected for its specificity for a particular target analyte. A variety of immunoassay formats may be used to select antibodies specifically reactive with a particular antigen. For example, solid-phase ELISA immunoassays are routinely used to select monoclonal antibodies specifically immunoreactive with an analyte. See Harlow and Lane (ANTIBODIES: A LABORATORY MANUAL, Cold Springs Harbor Publications, New York, (1988)) for a description of immunoassay formats and conditions that can be used to determine specific immunoreactivity. Typically a specific or selective reaction will be at least twice background signal to noise and more typically more than 10 to 100 times greater than background.

An "immunologically reactive fragment" of a protein refers to a portion of the protein or peptide that is immunologically reactive with a binding partner, e.g., an antibody, which is immunologically reactive with the protein itself.

Antibodies to *Trichomonas* proteins can be generated using methods that are well known in the art. Such antibodies can include, but are not limited to, polyclonal, monoclonal, chimeric, humanized, single chain, Fab fragments, and fragments produced by an expression library, including phage display. (See, e.g., Paul, FUNDAMENTAL IMMUNOLOGY, 3rd Ed., 1993, Raven Press, New York, for antibody structure and terminology.)

Antibody fragments that contain specific binding sites for a *Trichomonas* protein can also be generated. For example, such fragments include, but are not limited to, the $F(ab')_2$ fragments that can be produced by pepsin digestion of the antibody molecule, and the Fab fragments that can be generated by reducing the disulfide bridges of the $F(ab')_2$ fragments. Alternatively, Fab expression libraries can be constructed to allow rapid and easy identification of monoclonal Fab fragments with the desired specificity (Huse et al., *Science* 254, 1275-1281 (1989)).

For the production of antibodies, various hosts including goats, rabbits, rats, mice, humans, and others, may be immunized by injection with a *Trichomonas* protein (e.g., an α-actinin protein) or any fragment or oligopeptide or conjugate thereof that has immunogenic properties. Depending on the host species, various adjuvants can be used to increase the immunological response. Such adjuvants include, but are not limited to, Freund's complete and incomplete adjuvant, mineral gels such as aluminum hydroxide, and surface active substances such as lysolecithin, pluronic polyols, polyanions, peptides, oil emulsions, keyhole limpet hemocyanin, and dinitrophenol. Examples of adjuvants used in humans include BCG (bacilli Calmette-Guerin) and *Corynebacterium parvum*.

Monoclonal antibodies to *Trichomonas* proteins can be prepared using any technique that provides for the production of antibody molecules by continuous cell lines in culture. These include, but are not limited to, the hybridoma technique, the human B-cell hybridoma technique, and the EBV-hybridoma technique (Kohler et al. (1975) *Nature* 256:495-497; Kozbor et al. (1985) *J. Immunol. Methods* 81:31-42; Cote et al. (1983) *Proc. Natl. Acad. Sci.* 80:2026-2030; Cole et al. (1984) *Mol. Cell Biol.* 62:109-120). Briefly, the procedure can be as follows: an animal is immunized with a *Trichomonas* protein or immunogenic fragment or oligopeptide or conjugate thereof. For example, haptenic oligopeptides of a *Trichomonas* protein can be conjugated to a carrier protein to be used as an immunogen. Lymphoid cells (e.g., splenic lymphocytes) are then obtained from the immunized animal and fused with immortalizing cells (e.g., myeloma or heteromyeloma) to produce hybrid cells. The hybrid cells are screened to identify those that produce the desired antibody.

Human hybridomas that secrete human antibody can be produced by the Kohler and Milstein technique and according to art-known protocols. Hybridoma production in rodents, especially mouse, is a very well established procedure and thus, stable murine hybridomas provide an unlimited source of antibody of select characteristics. As an alternative to human antibodies, the mouse antibodies can be converted to chimeric murine/human antibodies by genetic engineering techniques. See Oi et al., *Bio Techniques* 4(4):214-221 (1986); Sun et al., *Hybridoma* 5 (1986).

The monoclonal antibodies of this invention specific for *Trichomonas* protein epitopes can also be used to produce anti-idiotypic (paratope-specific) antibodies. (See e.g., McNamara et al., *Science* 220, 1325-26 (1984); Kennedy et al., *Science* 232:220 (1986).) These antibodies resemble the *Trichomonas* protein epitope and thus can be used as an antigen to stimulate an immune response against the *Trichomonas* protein.

In addition, techniques developed for the production of "chimeric antibodies," the splicing of mouse antibody genes to human antibody genes to obtain a molecule with appropriate antigen specificity and biological activity can be used (Morrison et al. *Proc. Natl. Acad. Sci.* 81:6851-6855 (1984); Neuberger et al., *Nature* 312:604-608 (1984); Takeda et al., *Nature* 314:452-454 (1985)). Alternatively, techniques described for the production of single chain antibodies can be adapted, using methods known in the art, to produce *Trichomonas* protein-specific single chain antibodies. Antibodies with related specificity, but of distinct idiotypic composition, can be generated by chain shuffling from random combinatorial immunoglobin libraries (Burton, *Proc. Natl. Acad. Sci.* 88:11120-3 (1991)).

Antibodies can also be produced by inducing in vivo production in the lymphocyte population or by screening immunoglobulin libraries or panels of highly specific binding reagents as described in the literature (Orlandi et al., *Proc. Natl. Acad. Sci.* 86:3833-3837 (1989)); Winter et al., *Nature* 349:293-299 (1991)).

Various immunoassays can be used to identify antibodies of this invention having the desired specificity. Furthermore, a wide variety of immunoassays may be employed in the methods of this invention to detect antibodies and antigens of *Trichomonas* proteins for diagnosis of *Trichomonas* infection and to identify a subject with prostate cancer or a subject at increased risk of having or developing prostate cancer. Such immunoassays typically involve the measurement of antigen/antibody complex formation between a *Trichomonas* protein or peptide and its specific antibody.

The immunoassays of the invention can be either competitive or noncompetitive and both types of assays are well-known and well-developed in the art. In competitive binding assays, *Trichomonas* antigen or antibody competes with a detectably labeled *Trichomonas* antigen or antibody for specific binding to a capture site bound to a solid surface. The concentration of labeled antigen or antibody bound to the capture agent is inversely proportional to the amount of free antigen or antibody present in the sample.

Noncompetitive assays can be, for example, sandwich assays, in which the sample analyte (target antibody) is bound between two analyte-specific binding reagents. One of the binding agents is used as a capture agent and is bound to a solid surface. The other binding agent is labeled and is used to measure or detect the resultant antigen/antibody complex by e.g., visual or instrument means. A number of combinations of capture agent and labeled binding agent can be used. For instance, antigens derived from *Trichomonas* can be used as the capture agent and labeled anti-human antibodies specific for the constant region of human antibodies can be used as the labeled binding agent to detect antibodies in a sample that bind the *Trichomonas* antigen. Goat, sheep and other non-human antibodies specific for human immunoglobulin constant regions are well known in the art. Alternatively, the anti-human antibodies can be the capture agent and the antigen can be labeled. Other proteins capable of specifically binding human immunoglobulin constant regions, such as protein A, protein L or protein G can also be used as the capture agent or labeled binding agent. These proteins are normal constituents of the cell walls of streptococcal bacteria. They exhibit a strong nonimmunogenic reactivity with immunoglobulin constant regions from a variety of species. (See, e.g., Kronval et al., *J. Immunol.*, 111:1401-1406 (1973); Akerstrom et al., *J Immunol.*, 135:2589-2542 (1985).)

In some embodiments, the non-competitive assays need not be sandwich assays. For instance, the antibodies or antigens in the sample can be bound directly to the solid surface. The presence of antibodies or antigens in the sample can then be detected using labeled antigen or antibody, respectively.

In some embodiments, antibodies and/or *Trichomonas* proteins can be conjugated or otherwise linked or connected (e.g., covalently or noncovalently) to a solid support (e.g., bead, plate, slide, dish, membrane or well) in accordance with known techniques. Antibodies can also be conjugated or otherwise linked or connected to detectable groups such as radiolabels (e.g., $^{35}S$, $^{125}I$, $^{32}P$, $^{13}H$, $^{14}C$, $^{131}I$, enzyme labels (e.g., horseradish peroxidase, alkaline phosphatase), gold beads, chemiluminescence labels, ligands (e.g., biotin) and/or fluorescence labels (e.g., fluorescein) in accordance with known techniques.

A variety of organic and inorganic polymers, both natural and synthetic can be used as the material for the solid surface. Nonlimiting examples of polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that can be used include, but are not limited to, include paper, glass, ceramic, metal, metalloids, semiconductive materials, cements and the like. In addition, substances that form gels, such as proteins (e.g., gelatins), lipopolysaccharides, silicates, agarose and polyacrylamides can be used. Polymers that form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes can be employed depending upon the nature of the system.

A variety of immunoassay systems can be used, including but not limited to, radio-immunoassays (RIA), enzyme-linked immunosorbent assays (ELISA) assays, enzyme immunoassays (EIA), "sandwich" assays, gel diffusion precipitation reactions, immunodiffusion assays, agglutination assays, immunofluorescence assays, fluorescence activated cell sorting (FACS) assays, immunohistochemical assays, protein A immunoassays, protein G immunoassays, protein L immunoassays, biotin/avidin assays, biotin/streptavidin assays, immunoelectrophoresis assays, precipitation/flocculation reactions, immunoblots (Western blot; dot/slot blot); immunodiffusion assays; liposome immunoassay, chemiluminescence assays, library screens, expression arrays, etc., immunoprecipitation, competitive binding assays and immunohistochemical staining. These and other assays are described, among other places, in Hampton et al. (*Serological Methods, a Laboratory Manual*, APS Press, St Paul, Minn. (1990)) and Maddox et al. (*J. Exp. Med.* 158:1211-1216 (1993)).

The methods of this invention can also be carried out using a variety of solid phase systems, such as described in U.S. Pat. No. 5,879,881, as well as in a dry strip lateral flow system, such as described, for example, in U.S. Patent Publication No. 20030073147, the entire contents of each of which are incorporated by reference herein.

In addition, a nucleic acid having the nucleotide sequence or a substantially similar nucleotide sequence of the gene encoding a *Trichomonas* protein of this invention can be used as a probe in a nucleic acid hybridization assay for the detection of a *Trichomonas* protein in various tissues and/or body fluids of a subject of this invention. The probe can be used in any type of nucleic acid hybridization assay including Southern blots (Southern, 1975, *J. Mol. Biol.* 98:508), Northern blots (Thomas et al., 1980, *Proc. Natl Acad. Sci.* U.S.A. 77:5201-05), colony blots (Grunstein et al., 1975, *Proc. Natl Acad. Sci.* U.S.A. 72:3961-65), slot blots, dot blots, etc. Stringency of hybridization can be varied depending on the requirements of the assay according to methods well known in the art. Assays for detecting nucleic acid encoding a *Trichomonas* protein in a cell, or the amount thereof, typically involve first contacting the cells or extracts of the cells containing nucleic acids therefrom with an oligonucleotide probe that specifically binds to nucleic acid encoding a *Trichomonas* protein or peptide as described herein (typically under conditions that permit access of the oligonucleotide to intracellular material), and then detecting the presence or absence of binding of the oligonucleotide probe thereto. Any suitable assay format can be employed (see, e.g., U.S. Pat. No. 4,358, 535; U.S. Pat. Nos. 4,302,204; 4,994,373; 4,486,539; 4,563, 419; and 4,868,104, the disclosures of each of which are incorporated herein by reference in their entireties).

The antibodies of this invention can be used in in vitro, in vivo and/or in in situ assays to detect a *Trichomonas* protein or peptide of this invention.

Also as used herein, the terms peptide and polypeptide are used to describe a chain of amino acids, which correspond to those encoded by a nucleic acid. A peptide usually describes a chain of amino acids of from two to about 30 amino acids and polypeptide usually describes a chain of amino acids having more than about 30 amino acids. The term polypeptide can refer to a linear chain of amino acids or it can refer to a chain of amino acids, which have been processed and folded into a functional protein. It is understood, however, that 30 is an arbitrary number with regard to distinguishing peptides and polypeptides and the terms may be used interchangeably for a chain of amino acids around 30. The peptides and polypeptides of the present invention can be obtained by isolation and purification of the peptides and polypeptides from cells where they are produced naturally or by expression of a recombinant and/or synthetic nucleic acid encoding the peptide or polypeptide. The peptides and polypeptides of this invention can be obtained by chemical synthesis, by proteolytic cleavage of a polypeptide and/or by synthesis from nucleic acid encoding the peptide or polypeptide.

It is also understood that the peptides and polypeptides of this invention may also contain conservative substitutions where a naturally occurring amino acid is replaced by one having similar properties and which does not alter the function of the peptide or polypeptide. Such conservative substitutions are well known in the art. Thus, it is understood that, where desired, modifications and changes can be made in the nucleic acid and/or amino acid sequence of the peptides and polypeptides of the present invention and still obtain a peptide or polypeptide having like or otherwise desirable characteristics. Such changes can occur in natural isolates or can be synthetically introduced using site-specific mutagenesis, the procedures for which, such as mis-match polymerase chain reaction (PCR), are well known in the art. One of skill in the art will also understand that polypeptides and nucleic acids that contain modified amino acids and nucleotides, respectively (e.g., to increase the half-life and/or the therapeutic efficacy of the molecule), can be used in the methods of the invention.

"Nucleic acid" as used herein refers to single- or double-stranded molecules which may be DNA, comprised of the nucleotide bases A, T, C and G, or RNA, comprised of the bases A, U (substitutes for T), C, and G. The nucleic acid may represent a coding strand or its complement. Nucleic acids may be identical in sequence to a sequence that is naturally occurring or may include alternative codons that encode the same amino acid as that which is found in the naturally occurring sequence. Furthermore, nucleic acids may include codons that represent conservative substitutions of amino acids as are well known in the art. The nucleic acids of this invention can also comprise any nucleotide analogs and/or derivatives as are well known in the art.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by well-known techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

The nucleic acid encoding the peptide or polypeptide of this invention can be part of a recombinant nucleic acid construct comprising any combination of restriction sites and/or functional elements as are well known in the art that facilitate molecular cloning and/or other recombinant DNA manipulations. Thus, the present invention further provides a recombinant nucleic acid construct comprising a nucleic acid encoding a peptide and/or polypeptide of this invention.

The present invention further provides a vector comprising a nucleic acid encoding a peptide and/or polypeptide of this invention. The vector can be an expression vector which contains all of the genetic components required for expression of the nucleic acid in cells into which the vector has been introduced, as are well known in the art. The expression vector can be a commercial expression vector or a viral vector and/or it can be constructed in the laboratory according to standard molecular biology protocols. The expression vector can comprise, for example, viral nucleic acid including, but not limited to, vaccinia virus, adenovirus, retrovirus, alphavirus and/or adeno-associated virus nucleic acid. The nucleic acid or vector of this invention can also be in a liposome or a delivery vehicle, which can be taken up by a cell via receptor-mediated or other type of endocytosis.

The nucleic acid of this invention can be in a cell, which can be a cell expressing the nucleic acid whereby a peptide and/or polypeptide of this invention is produced in the cell. In addition, the vector of this invention can be in a cell, which can be a cell expressing the nucleic acid of the vector whereby a peptide and/or polypeptide of this invention is produced in the cell. It is also contemplated that the nucleic acids and/or vectors of this invention can be present in a host (e.g., a bacterial cell, a cell line, a transgenic animal, etc.) that can express the peptides and/or polypeptides of the present invention.

In some embodiments, for recombinant production of the chimeric polypeptides and/or peptides of this invention in prokaryotes, there are numerous *E. coli* (*Escherichia coli*) expression vectors known to one of ordinary skill in the art useful for the expression of nucleic acid encoding proteins or peptides of this invention. Other microbial hosts suitable for use include bacilli, such as *Bacillus subtilis*, and other enterobacteria, such as *Salmonella, Serratia*, as well as various *Pseudomonas* species. These prokaryotic hosts can support expression vectors that will typically contain sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence and have ribosome binding site sequences for example, for initiating and completing transcription and translation. If necessary, an amino terminal methionine can be provided by insertion of a Met codon 5' and in-frame with the coding sequence of the protein. Also, the carboxy-terminal extension of the protein can be removed using standard oligonucleotide mutagenesis procedures.

Additionally, yeast expression systems and baculovirus systems, which are well known in the art, can be used to produce the chimeric peptides and polypeptides of this invention.

The vectors of this invention can be transferred into a cell by well-known methods, which vary depending on the type of cell host. For example, calcium chloride transfection is commonly utilized for prokaryotic cells, whereas calcium phosphate treatment, lipofection or electroporation can be used for other cell hosts.

The present invention further provides a kit for detection of alpha actinin antibodies and/or proteins of this invention. Such a kit can comprise one or antibodies of this invention, along with suitable buffers, wash solutions, dilution buffers, secondary antibodies, detection reagents, etc. for the detection of antigen/antibody complex formation under various conditions. In another embodiment, a kit of this invention can comprise a polypeptide, a peptide, an antigenic fragment and/or a fusion protein or peptide comprising an alpha actinin epitope, along with suitable buffers, wash solutions, dilution buffers, secondary antibodies, detection reagents, etc. for the detection of antigen/antibody complex formation under various conditions.

The present invention is more particularly described in the Examples set forth below, which are not intended to be limiting of the embodiments of this invention.

EXAMPLES

Studies Demonstrating Correlation Between *Trichomonas* Infection and Prostate Cancer A large nested case-control study of the sexually transmitted (STI) infection by *Trichomonas vaginalis* and for association with prostate cancer was carried out among participants in the Health Professionals Follow-up Study (HPFS). The existence of exposure to this STI was established by the detection of specific serum IgG antibody to a very immunogenic protein of the organism. In this study, the sera from men was obtained prior to prostate cancer diagnosis, which served to establish a temporal relationship between STI and carcinogenesis. The particular immunogenic protein called α-actinin was chosen because of established antibody presence among infected women and because of the possibility of detecting antibody in men who overall experience reduced or absent symptomatology from this STI. This, therefore, means that symptoms of unrecognized origin and/or this STI without symptoms in men might be detected.

In this large HPFS begun in 1986 a large number (51,529) of men were enrolled for prospective follow-up analysis. The men participated in questionnaires every two to four years depending on the questions addressed. Of these a total of 18,018 men gave blood samples for evaluation. Blood was fractionated, and plasma was collected for storage and future research. Prostate cancer diagnoses were from biennial follow-up questionnaires. Prostate cancer diagnoses and/or deaths were also derived from the National Death Index, the US Postal Service, or the next of kin. Importantly for correlations with anti-*T. vaginalis* IgG antibody, diagnoses of and/or deaths due to prostate cancer were confirmed by medical record and pathology report review with permission from the participant or the next of kin.

With the exception of non-melanoma skin cancer, men between the years 1993-95 free of cancer at the time of blood draw were eligible for inclusion in the nested case-control study. Cases were all men diagnosed with prostate cancer (except stage T1a) between the date of blood draw and Jan. 31, 2000 (n=691). Significantly, participants diagnosed with stage T1a prostate cancer were not included as their tumors comprise ≦5% of resected prostate tissue that may be prone to detection bias. For this study, men with at least one PSA test after blood draw indicated above and free of cancer and alive at time of diagnosis served as controls. Importantly, controls were matched by age, year, time (midnight-9 a.m., 9 a.m.-noon, noon to before 4 p.m., and 4 p.m.-midnight) and season (January to March; April to June; July to September; and October to December) of blood draw in 1993-5, and PSA testing history prior to 1993-5 (yes/no).

IgQ antibody to the α-actinin present in plasma was detected by a standard enzyme-linked immunosorbent assay (ELISA). The format for the ELISA included bound recombinant α-actinin protein purified from lysate of the bacteria used to produce the protein. For comparison purposes, an ELISA utilizing the complex lysate derived from a fresh clinical *T. vaginalis* isolate called T016 was employed. This complex lysate gave results with reduced sensitivity and increased nonspecific binding properties thereby making this lysate-ELISA non-reproducible.

The recombinant *T. vaginalis* α-actinin protein was prepared using standard protocols. A single *Escherichia coli* XL1-Blue (Stratagene, La Jolla, Calif.) colony containing a recombinant plasmid with the full-length α-actinin gene was inoculated into 200 mL of LB medium. The colony was then incubated for 5 h at 37° C., after which the bacteria were induced with 1.0 mM isopropyl-β-D-thiogalactopyranoside (IPTG) for 3 h. After centrifugation, the pelleted bacteria were washed with 50 mM Tris-HCl, pH 8.0, suspended in lysis buffer (62.5 mM Tris-HCl, pH 6.8 containing 2% SDS, 10% glycerol, and 2% β-mercaptoethanol), and boiled for five minutes. Insoluble debris from lysates was removed by centrifugation at 6,500× g. The clarified lysate was fractionated by continuous elution electrophoresis (Model 491 Pre Cell, BIO-RAD, Hercules, Calif.), and the fraction containing purified recombinant α-actinin protein detected by dot-blot-immunoassays using a monoclonal antibody (mAb) called HA423. Fractions with purified single-band protein reactive with mAb were pooled and dialyzed against 10 mM Tric-HCl, pH 8.0. Protein concentrations were measured by the Bradford Assay, and adjusted to 20 μg/ml with 50 mM sodium carbonate buffer (5.229 g $Na_2CO_3$, 4.2 g of $NHCO_3$ in double-distilled water, pH 9.6).

Ninety-six well ELISA plates (MAXISORP Immuno Module; NUNC, Roskilde, Denmark) were coated with 100 μL (2 μg protein) per well of diluted recombinant protein, and incubated overnight at 4° C. The plates were then washed three times with PBS-Tween-20 (0.05% Tween-20 in PBS, pH 7.0), followed by the addition of 200 μL per well of blotting buffer (10% skim milk in PBS). After incubation at RT for 1 h, the plates were washed once with PBS-Tween-20 and either used immediately or air-dried at RT and stored at 4° C. Plasma samples were diluted 1:25 (v/v) in PBS-Tween-20 containing 10% skim milk, and 100 μL of this dilution was added to each well. After 2 h at 37° C., the plates were washed 3 times with PBS-Tween-20 followed by addition of 100 μL secondary goat anti-human IgG (Fab fragment) conjugated to horseradish peroxidase diluted 1:5,000 in PBS. After an additional 2 h incubation at 37° C., plates were washed 3 times with PBS-Tween-20. Color development followed addition of 100 μL of substrate solution (ABTS; phosphate-citrate buffer with 0.03% sodium perborate; Sigma Chemical Co., St. Louis, Mo.) and incubation of plates at RT for 15 min. Optical densities (OD) were from examining supernatants at absorbance of 405 nm using an ELISA reader (Bio-TEK Instruments, Inc., Winooski, Vt.).

All prostate cancer case and control samples were tested in duplicate (OD intra-assay coefficient of variation=14%). OD scores were assigned to each sample based on the mean duplicate OD value (0: OD<0.150; 1+: 0.150≦OD<0.250; 2+: 0.250≦OD<0.500; 3+: 0.500≦OD<1.000; 4+: OD≧1.000). All samples with scores 1+ through 4+ were retested in duplicate and observed to have the same OD score. Samples with high 2+ OD scores (0.400≦OD<0.500) were considered indicative of a history of trichomonosis, and those with 3+ or 4+ OD scores (OD≧0.500) were considered highly indicative of a history of trichomonosis based on expert opinion without knowledge of prostate cancer status. When an OD cut-point of 0.400 was used to define seropositivity, the observed agreement between duplicate samples was 0.73, as measured by kappa. Samples were tested in random case-control pair order, with case and matching control samples adjacent to one another, but in random within-pair order, and laboratory technicians blinded to the case-control status of each sample. Assay reliability was assessed by including two blinded seropositive and seronegative samples in the testing sequence for each plate (kappa=0.79). Samples of known serostatus were used as opposed to duplicate samples because of the low expected seroprevalence of trichomonosis in this population.

Although prostate cancer cases and controls had similar mean and median anti-*T. vaginalis* IgG levels, a borderline significantly greater proportion of cases had high OD scores (OD≧0.400, 12.6%) than controls (9.4%, OR=1.41, 95% CI: 0.99-2.00). Similar results were observed after adjustment for potentially confounding variables, including histories of other STIs, and for organ-confined, low-grade and high-grade prostate cancer. Additionally, a statistically significant positive association was observed among men with a family history of prostate cancer, whereas a much weaker association was observed among men without such a history.

In summary, an examination of serum IgG antibody in men in this large study showed a borderline significant positive association between the STI caused by *T. vaginalis* and prostate cancer. This relationship was found across numerous variables, including, for example, the early stage, and low and high grades of prostate cancer, and after adjustment for a history of other STIs, STI correlates and prostate cancer risk factors. Particularly noteworthy was the strong association between this STI and among men who never used aspirin and men with a family history of prostate cancer.

Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference into this application in order to more fully describe the state of the art to which this invention pertains.

What is claimed is:

1. A method of identifying a human male subject as having an increased risk of developing prostate cancer, comprising:
   a) contacting a sample from the subject with a *Trichomonas vaginalis* α-actinin protein under conditions whereby an antigen/antibody complex can form; and
   b) detecting formation of an antigen/antibody complex, thereby detecting an antibody that specifically binds a *Trichomonas vaginalis* α- actinin protein in the sample and thereby identifying the subject as having an increased risk of developing prostate cancer.

2. The method of claim 1, wherein the sample is serum.

3. The method of claim 1, wherein the sample is saliva.

4. The method of claim 1, wherein the subject has a family history of prostate cancer.

* * * * *

UNITED STATES PATENT AND TRADEMARK OFFICE
CERTIFICATE OF CORRECTION

PATENT NO.        : 7,439,028 B2  
APPLICATION NO.   : 11/519708  
DATED             : October 21, 2008  
INVENTOR(S)       : Alderete et al.

Page 1 of 1

It is certified that error appears in the above-identified patent and that said Letters Patent is hereby corrected as shown below:

Column 10, Line 63:    Please correct "IgQ antibody"  
                                   To read -- IgG antibody --

Signed and Sealed this

Twenty-fourth Day of February, 2009

JOHN DOLL  
*Acting Director of the United States Patent and Trademark Office*